United States Patent
Engleman et al.

(10) Patent No.: US 6,821,778 B1
(45) Date of Patent: Nov. 23, 2004

(54) METHODS FOR USING DENDRITIC CELLS TO ACTIVATE GAMMA/DELTA-T CELL RECEPTOR-POSITIVE T CELLS

(75) Inventors: Edgar G. Engleman, Atherton, CA (US); Anita Mehta, Mountain View, CA (US); Masaru Takamizawa, Mountain View, CA (US); Francesco Fagnoni, Mountain View, CA (US); Sergiusz Markowicz, Warszawa (PL)

(73) Assignee: The Board of Trustees of Leland Stanford Junior University, Stanford, CA (US)

( * ) Notice: Subject to any disclaimer, the term of this patent is extended or adjusted under 35 U.S.C. 154(b) by 0 days.

(21) Appl. No.: 08/610,195

(22) Filed: Feb. 28, 1996

Related U.S. Application Data

(63) Continuation of application No. 08/160,571, filed on Dec. 1, 1993, now abandoned.

(51) Int. Cl.$^7$ .............................. C12N 5/08; C12N 5/00; G01N 33/53

(52) U.S. Cl. .................. 435/372.3; 435/7.24; 435/372; 435/373

(58) Field of Search ............................. 435/7.24, 372.3, 435/373, 372, 2, 240.1, 240.02, 240.21, 7.2; 424/184.1, 277.1, 204.1, 208.1, 243.1, 248.1, 93.7, 93.71; 514/924

(56) References Cited

U.S. PATENT DOCUMENTS 5,679,347 A * 10/1997 Porcelli et al.

OTHER PUBLICATIONS

Kabelito Crit. Rev. Immunol. 11: 281–303 (1992).*
Vandekerckhove et al. J. Immunol. 144: IL88. 1294(1990).*
Zocchi et al. Eur. J. Immunol. 20: 2685–2689 (1990).*
Macatonia et al. Immunol. 74: 399–406 (1991).*
Haas Ann Rev Immunol. 11:637–85 (1993).*
Lotze Cell Transplantation 2: 33–47 (1993).*
Pancholi, P. et al. Immunology 76: 217–224, Jun. 1992.*
Bhardwaj, N. et al. J. Exp. Med. 175: 267–273, Jan. 1993.*
Macatonia, S. E. et al. Immunology 74: 399–406, Nov. 1991.*
Harada, Y. et al. Jpn. J. Cancer Res. 80: 988–992, Oct. 1989.*
Urban, J. L. et al. Annu. Rev. Immunol. 10: 617–644, 1994.*
Inaba, k. et al. J. Exp. Med. 172: 631–640, Aug. 1990.*
Bujdoso, R. et al. Intern. Rev. Immunol. 6: 177–186, 1990.*
Morita, C. et al. Eur. J. Immunol. 21 (12): 2999–3007, Dec. 1991.*

* cited by examiner

Primary Examiner—Hankyel T. Park
(74) Attorney, Agent, or Firm—Peter J. Dehlinger; Perkins Coie LLP

(57) ABSTRACT

This invention relates to methods of using human dendritic cells to present antigens for the induction of antigen-specific T cell-mediated immune responses. In particular, it relates to the isolation of dendritic cells from human blood, exposing the cells to antigens, co-culturing the antigen-pulsed dendritic cells with γδ-T cell receptor-positive-T cells (γδ-TCR$^+$ T cells) obtained from unprimed or weakly primed individuals for the stimulation of antigen-specific T cell proliferative and cytotoxic activities. The dendritic cell antigen presentation system described herein has a wide range of applications, including but not limited to, activation and expansion of large numbers of antigen-specific major histocompatibility complex-unrestricted T cells for use in adoptive cellular immunotherapy against infectious diseases and cancer.

11 Claims, 9 Drawing Sheets

Figure 1A:
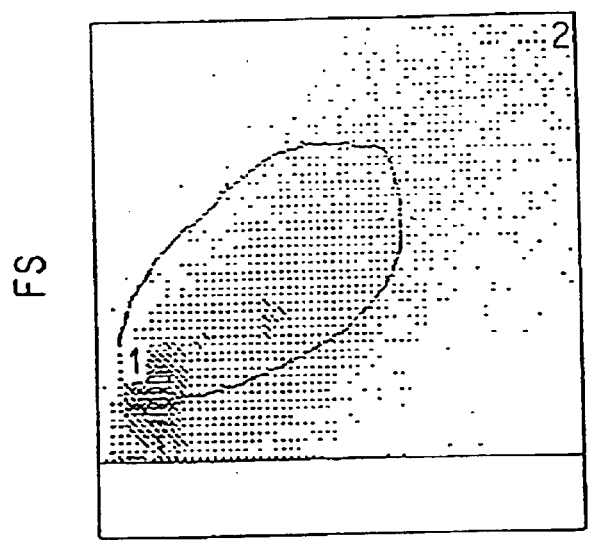

|  | MIN | MAX | COUNT | PERCENT | MEAN | SD | % HPCV |
|---|---|---|---|---|---|---|---|
| 2 X | 0 | 63 | 9880 | 100.0 | 20.2 | 16.2 | 31.6 |
| Y | 9 | 63 | | | 25.5 | 14.1 | |

|  | MIN | MAX | COUNT | PERCENT | MEAN | SD | % HPCV |
|---|---|---|---|---|---|---|---|
| 1 | 2.705 | 1023. | 4315 | 86.3 | 112.5 | 0.5 | |

| | MIN | MAX | COUNT | PERCENT | MEAN | SD | % HPCV |
|---|---|---|---|---|---|---|---|
| 2 X | 0 | 63 | 9880 | 100.0 | 20.2 | 16.2 | 31.6 |
| Y | 9 | 63 | | | 25.5 | 14.1 | |

| | MIN | MAX | COUNT | PERCENT | MEAN | SD | % HPCV |
|---|---|---|---|---|---|---|---|
| 1 | 2.705 | 1023. | 4315 | 86.3 | 112.5 | 0.5 | |

|     | MIN   | MAX   | COUNT | PERCENT | MEAN | SD   | % HPCV |
|-----|-------|-------|-------|---------|------|------|--------|
| 2 X | 0     | 63    | 7040  | 100.0   | 19.9 | 12.4 | 27.5   |
| Y   | 9     | 63    |       |         | 23.2 | 10.6 | 18.7   |

|   | MIN    | MAX   | COUNT | PERCENT | MEAN  | SD  | % HPCV |
|---|--------|-------|-------|---------|-------|-----|--------|
| 1 | 1.024  | 1023. | 5476  | 93.1    | 118.7 | 0.3 | 3.95   |
| 2 | 18.88  | 1023. | 5092  | 86.6    | 151.1 | 0.2 | 3.95   |

|   | MIN | MAX | COUNT | PERCENT | MEAN | SD | % HPCV |
|---|---|---|---|---|---|---|---|
| 2 X | 0 | 63 | 10879 | 100.0 | 23.5 | 16.0 | |
| Y | 7 | 63 | | | 33.3 | 14.7 | |

|   | MIN | MAX | COUNT | PERCENT | MEAN | SD | % HPCV |
|---|---|---|---|---|---|---|---|
| 1 | 1.271 | 1023. | 4968 | 99.4 | 99.12 | 0.34 | 5.28 |

METHODS FOR USING DENDRITIC CELLS TO ACTIVATE GAMMA/DELTA-T CELL RECEPTOR-POSITIVE T CELLS

This is a continuation of application Ser. No. 08/160,571, filed Dec. 1, 1993, now abandoned.

1. INTRODUCTION

This invention relates to methods of using human dendritic cells to present antigens for the induction of antigen-specific T cell-mediated immune responses. In particular, it relates to the isolation of dendritic cells from human blood, exposing the cells to antigens, co-culturing the antigen-pulsed dendritic cells with γδ-T cell receptor-positive-T cells (γδ-TCR$^+$ T cells) obtained from unprimed or weakly primed individuals for the stimulation of antigen-specific T cell proliferative and cytotoxic activities. The dendritic cell antigen presentation system described herein has a wide range of applications, including but not limited to, activation and expansion of large numbers of antigen-specific major histocompatibility complex-unrestricted T cells for use in adoptive cellular immunotherapy against infectious diseases and cancer.

2. BACKGROUND OF THE INVENTION

2.1. Generation of an Immune Response

The introduction of a foreign antigen into an individual elicits an immune response consisting of two major components, the cellular and humoral immune responses, mediated by two functionally distinct populations of lymphocytes known as T and B cells, respectively. The T cells nay be further divided into two subsets by function and phenotype. A subset of T cells responds to antigen stimulation by producing lymphokines which "help" or activate various other cell types in the immune system. Another T cell subset is capable of developing into antigen-specific cytotoxic effector cells, being able to directly kill antigen-positive target cells. On the other hand, the B cell response is primarily carried out by secretory proteins, antibodies, which directly bind and neutralize antigens.

Helper T cells (TH) can be distinguished from classical cytotoxic T lymphocytes (CTL) and B cells by their cell surface expression of a glycoprotein marker termed CD4. Although the mechanism by which CD4$^+$ TH function has not been fully elucidated, the existence of functionally distinct subsets within the CD4$^+$ T cell compartment has been reported (Mosmann and Coffman, 1989, Ann. Rev. Immunol. 7:145–173). In the mouse, type 1 helper T cells (TH1) produce interleukin-2 (IL-2) and γ-interferon (γ-IFN) upon activation, while type 2 helper T cells (TH2) produce IL-4 and IL-5. Based on the profile of lymphokine production, TH1 appear to be involved in promoting the activation and proliferation of other T cell subsets including CTL, whereas TH2 specifically regulate B cell proliferation and differentiation, antibody synthesis, and antibody class switching. Some CD4$^+$ T cells, like CD8$^+$ CTL, appear to be capable of cytotoxic effector function.

A second T cell subpopulation is the classical CTL which express the CD8 surface marker. Unlike most TH, these cells display cytolytic activity upon direct contact with target cells, although they are also capable of producing certain lymphokines. In vivo, CTL function is particularly important in situations where an antibody response alone is inadequate. There is a preponderance of experimental evidence that CTL rather than B cells and their antibody products play a principal role in the defense against viral infections and cancer.

A salient feature of both T and B cell responses is their exquisite specificity for the immunizing antigen; however, the mechanisms for antigen recognition differ between these two cell types. B cells recognize antigens by antibodies, either acting as cell surface receptors or as secreted proteins, which bind directly to antigens on a solid surface or in solution, whereas T cells only recognize antigens that have been processed or degraded into small fragments and presented on a solid phase such as the surface of antigen-presenting cells (APC). Additionally, antigenic fragments must be presented to T cells in association with major histocompatibility complex (MHC)-encoded class I or class II molecules. The MHC refers to a cluster of genes that encode proteins with diverse immunological functions. In man, the MHC is known as HLA. Class I gene products are found on all somatic cells, and they were originally discovered as targets of major transplantation rejection responses. Class II gene products are mostly expressed on cells of various hematopoietic lineages, and they are involved in cell-cell interactions in the immune system. Most importantly, MHC-encoded proteins have been shown to function as receptors for processed antigenic fragments on the surface of APC (Bjorkman et al., 1987, Nature 329: 506–512).

Another level of complexity in the interaction between a T cell expressing an αβ-T cell receptor and an antigenic fragment is that it occurs only if the MHC molecules involved are the same on the APC and the responding T cells. In other words, a T cell specific for a particular antigenic epitope expresses a receptor having low affinity for self MHC proteins, which when such MHC proteins on APC are occupied by the epitope, engage the T cell in a stronger interaction leading to antigen-specific T cell activation. The phenomenon of a T cell reacting with a processed antigen only when presented by cells expressing a matching MHC is known as MHC-restriction. This requirement presents a practical limitation to the use of MHC-restricted T cells in cellular immunotherapy since the T cells must be matched at the MHC with a recipient's target cells for them to be effective.

The specificity of T cell immune responses for antigens is a function of the unique receptors expressed by these cells. The T cell receptor (TCR) is structurally homologous to an antibody; it is a heterodimer composed of disulfide-linked glycoproteins. Four TCR polypeptide chains known as α, β, γ, and δ have been identified, although the vast majority of functional T cells including both CD4$^+$ T$_H$ and CD8$^+$ CTL, express the αβ heterodimeric TCR. Transfer of α and β genes alone into recipient cells was shown to be both necessary and sufficient to confer antigen specificity and MHC-restriction (Dembic et al., 1986, Nature 320: 232–238). Thus, the αβ TCR appears to be responsible for recognizing a combination of antigenic fragment and MHC determinants. In this regard, the ability of an antibody specific for MHC class I or class II molecules to inhibit the antigen reactivity of a particular T cell population is often used as an indication that the T cells express αβ-TCR.

The apparent basis of MHC restriction is that CD4$^+$ T cells express αβ TCR which recognize antigenic fragments physically associated with MHC class II proteins, while the TCR on CD8$^+$ CTL recognize MHC class I-associated fragments. Thus, CD4$^+$ T cells can recognize only a restricted class of APC that are class II$^+$, whereas CD8$^+$ CTL can interact with virtually any antigen-positive cells, since all somatic cells express class I molecules. CD4$^+$ CTL have been identified, and they are MHC class II restricted, and lyse target cells only if the latter express self-MHC class II determinants associated with specific antigenic fragments. Both CD4 and CD8 molecules also contribute to this interaction by binding to monotypic determinants on the MHC class II and I molecules, respectively.

A second type of TCR composed of γδ heterodimers is expressed by a small percentage of T cells. Approximately 10% of T cells in the peripheral blood express the γδ-TCR, and a larger percentage of T cells in certain epithelial tissues such as the gut and skin are reported to be γδ-positive (Allison and Havran, 1991, Annu. Rev. Immunol. 9:679–705). Although γδ-TCR$^+$ T cells differentiate in the thymus and appear to be able to respond to foreign antigens in a manner analogous to αβ-TCR-bearing T cells, the physiologic role of γδ-T cells is poorly understood. Some studies have shown that functionally active γδ-T cells can be cytolytic in an MHC unrestricted manner. If so, it may be possible to utilize antigen-specific γδ-TCR$^+$ T cells generated from one individual to treat another individual who is not MHC compatible with the donor. However, since there is a relatively small number of germ line gene segments encoding the γδ-TCR, the functional repertoire of γδ-T cells is unknown. The γδ-T cells are often referred to as being double negative because they lack the expression of CD4 and CD8 markers.

In summary, the generation of an immune response begins with the sensitization of CD4$^+$ and CD8$^+$ T cell subsets through their interaction with APC that express MHC-class I or class II molecules associated with antigenic fragments. The sensitized or primed CD4$^+$ T cells produce lymphokines that participate in the activation of B cells as well as various T cell subsets. The sensitized CD8$^+$ T cells increase in numbers in response to lymphokines and are capable of destroying any cells that express the specific antigenic fragments associated with matching MHC-encoded class I molecules. For example, in the course of a viral infection, CTL eradicate virally-infected cells, thereby limiting the progression of virus spread and disease development.

2.2. Antigen Presenting Cells

The presentation of antigens to T cells is carried out by specialized cell populations referred to as antigen presenting cells (APC). Typically, APC include macrophages/monocytes, B cells, and bone marrow-derived dendritic cells (DC). DC are sometimes also referred to as "professional" APC. APC are capable of internalizing exogenous antigens, cleaving them into smaller fragments in enzyme-rich vesicles, and coupling the fragments to MHC-encoded class I or class II products for expression on the cell surface (Goldberg and Rock, 1992, Nature 357:375–379). Since APC express both MHC-encoded class I and class II glycoproteins, they can present antigenic fragments to both CD4$^+$ and CD8$^+$ T cells for the initiation of an immune response.

By definition, APC not only can present antigens to T cells with antigen-specific receptors, but can provide all the signals necessary for T cell activation. Such signals are incompletely defined, but probably involve a variety of cell surface molecules as well as cytokines or growth factors. Further, the factors necessary for the activation of naive or unprimed T cells may be different from those required for the re-activation of previously primed memory T cells. The ability of APC to both present antigens and deliver signals for T cell activation is commonly referred to as an accessory cell function. Although monocytes and B cells have been shown to be competent APC, their antigen presenting capacities in vitro appear to be limited to the re-activation of previously sensitized T cells. Hence, they are not capable of directly activating functionally naive or unprimed T cell populations.

Although it had been known for a long time that APC process and present antigens to T cells, it was not shown until relatively recently that small antigenic peptides could directly bind to MHC-encoded molecules (Babbit et al., 1985, Nature 317: 359; Townsend et al., 1986, Cell 44: 959). However, it is believed that normally, complex antigens are proteolytically processed into fragments inside the APC, and become physically associated with the MHC-encoded proteins intracellularly prior to trafficking to the cell surface as complexes. Two distinct pathways for antigen presentation have been proposed (Braciale et al., 1987, Immunol. Rev. 98: 95–114). It was thought that exogenous antigens were taken up by APC, processed and presented by the exogenous pathway to class II restricted CD4$^+$ T cells, while the endogenous pathway processed intracellularly synthesized proteins, such as products of viral genes in virally-infected cells, for association with MHC class I proteins and presentation to CD8$^+$ CTL. However, although the two pathways in antigen processing and presentation may still be correct in some respects, the distinction is blurred in light of recent findings that exogenously added antigens may also be presented to class I-restricted CTL (Moore et al., 1988, Cell 54: 777). Since most studies of antigen presentation and T cell activation have utilized αβ-TCR$^+$ T cells, it is still not known how γδ-TCR$^+$ T cells recognize and respond to antigens, especially in light of the finding that they may react with antigens in an MHC-unrestricted manner. Nor is it clear whether only certain types of APC are capable of presenting antigens to γδ-T cells and whether naive unprimed γδ-T cells can be activated by antigen-pulsed APC in vitro.

The term "dendritic cells" refers to a diverse population of morphologically similar cell types found in a variety of lymphoid and non-lymphoid tissues (Steinman, 1991, Ann. Rev. Immunol. 9:271–296). These cells include lymphoid DC of the spleen, Langerhans cells of the epidermis, and veiled cells in the blood circulation. Although they are collectively classified as a group based on their morphology, high levels of surface MHC class II expression, and absence of certain other surface markers expressed on T cells, B cells, monocytes, and natural killer cells, it is presently not known whether they derive from a common precursor or can all function as APC in the same manner. Further, since the vast majority of published reports have utilized DC isolated from the mouse spleen, results from these studies may not necessarily correlate with the function of DC obtained from other tissue types. (Inaba et al., 1987, J. Exp. Med. 166:182–194; Hengel et al., 1987 J. Immunol., 139:4196–4202; Kast et al., 1988, J. Immunol., 140:3186–3193; Romani et al., 1989, J. Exp. Med. 169:1169–1178; Macatonia et al., 1989, J. Exp. Med. 169:1255–1264; Inaba et al., 1990, J. Exp. Med. 172:631–6640). For example, despite high levels of MHC-class II expression, mouse epidermal Langerhans cells, unlike splenic DC, are not active APC in mixed leucocyte reaction (MLR), unless cultured with granulocyte-macrophage colony stimulating factor (GM-CSF) (Witmer-Pock et al., 1987, J. Exp. Med. 166:1484–1498; Heufler et al., 1988, J. Exp. Med. 167:700–705). Most human Langerhans cells express the CD1 and CD4 markers, while freshly isolated blood DC express CD4 weakly, but not CD1. On the other hand, cultured peripheral blood DC express CD1c, but not CD4. Additionally, it has not been established the extent to which the functional characteristics observed with mouse DC are applicable to human DC, especially the DC obtained from non-splenic tissues; in part, due to inherent differences between the human and murine immune systems.

Recently, a few studies have described the isolation of human DC from the peripheral blood. (Young and Steinman, 1990, J. Exp. Med. 171:1315–1332; Freudenthal and Steinman, 1990, Proc. Natl. Acad. Sci. USA 87:7698–7702; Macatonia et al., 1989, Immunol. 67:285–289; Markowicz and Engleman, 1990, J. Clin. Invest. 85:955–961). However, all reported isolation procedures invariably involve the use of sheep red blood cells and/or fetal calf serum, which are potentially immunogenic foreign antigens that can be presented by DC to T cells, and if so, would interfere with the antigen-specific responses desired. Most importantly, it has not been determined prior to Applicants' invention whether human DC can, in fact, present exogenous antigens to $\gamma\delta$-TCR$^+$ T cells because human DC have only been tested as APC for $\alpha\beta$-TCR$^+$ T cells. Furthermore, human DC which are active in MLR or in presenting antigens to primed-$\alpha\beta$-T cells have not been shown to be capabl of presenting exogenous antigens for primary T cell activation.

3. SUMMARY OF THE INVENTION

The present invention relates to the isolation of human DC from the peripheral blood, their use as APC for the activation of primary and secondary $\gamma\delta$-TCR$^+$ T cell responses, and an in vitro method for assessing immune responsiveness of both unprimed and primed individuals to potentially immunogenic epitopes using DC as APC, and $\gamma\delta$-TCR$^+$ T cells as responders. Because DC are present at extremely low quantities in the human peripheral blood, their enrichment and purification are necessary in order to obtain adequate numbers for pulsing with antigens for the induction of both proliferative and cytotoxic $\gamma\delta$-TCR$^+$ T cell-mediated responses in vitro.

The invention is based, in part, on Applicants' discovery that DC partially purified from human blood by sequential density gradient centrifugation function as potent APC for the sensitization of autologous naive $\gamma\delta$-TCR$^+$ T cells. As shown in the working example described herein in Example 7, infra, DC exposed to HIV envelope and gag peptides in vitro activate primary antigen-specific $\gamma\delta$-TCR$^+$ T cell cytotoxic responses, while similarly prepared autologous monocytes are not effective. The $\gamma\delta$-T cell reactivity is not inhibited by antibodies to MHC class I and class II molecules, indicating that the T cells mediate cytotoxic activity in an MHC-unresricted manner. Additionally, $\gamma\delta$-TCR$^+$ T cells specific for *Mycobacterium tuberculosis* and for *Staphylococcus aureus* enterotoxin-A superantigen (SAE-A) have been generated using a similar procedure, and the T cells are shown to be capable of proliferating in response to the specific antigen. The anti-*M. tuberculosis* response is inhibited by antibodies to MHC class II determinants and to the CD1c molecule.

A wide variety of uses for this antigen presentation system is encompassed by the invention described herein, including but not limited to, the activation and expansion of antigen-specific $\gamma\delta$-TCR$^+$ T cells in vitro for use in adoptive cellular immunotherapy of infectious diseases and cancer, and the identification of antigenic epitopes for vaccine development. In particular, since the cytotoxic activity of the $\gamma\delta$-T cells described herein is antigen specific but MHC unrestricted, these cells may be especially useful in immunotherapy without the need of matching the donor effector cells with the MHC of a recipient.

4. BRIEF DESCRIPTION OF THE DRAWINGS

Figure 1B:
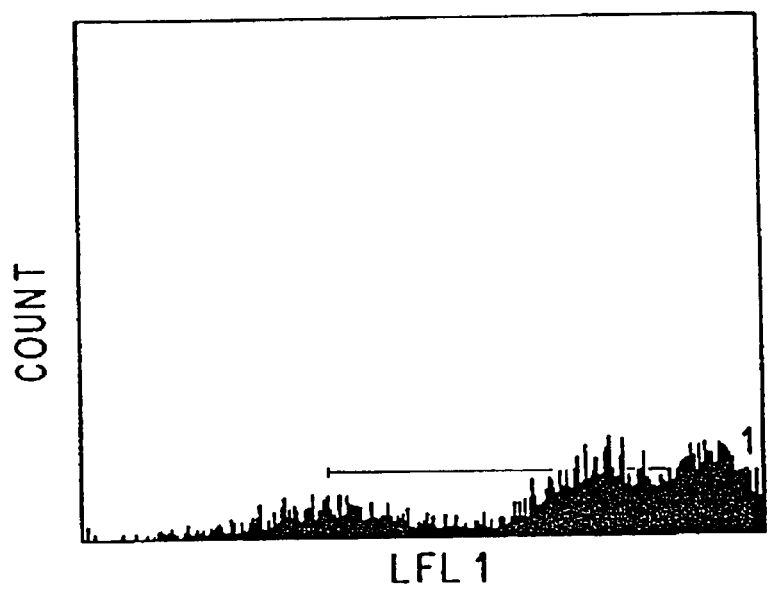

FIGS. 1A and 1B Cytofluorographic analysis of DC stained with antibodies after the first "NYCOPREP 1.068" discontinuous centrifugation.

Figure 2A:
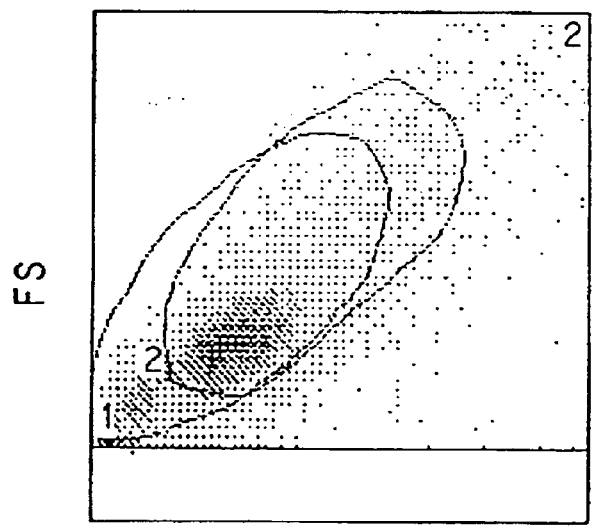
Figure 2B:
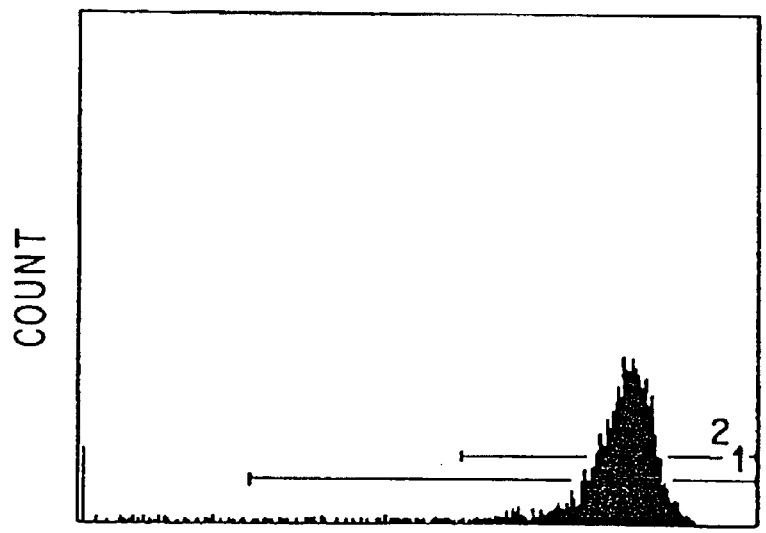

FIGS. 2A and 2B Cytofluorographic analysis of DC stained with antibodies after the second "NYCOPREP 1.068" discontinuous centrifugation.

Figure 3A:
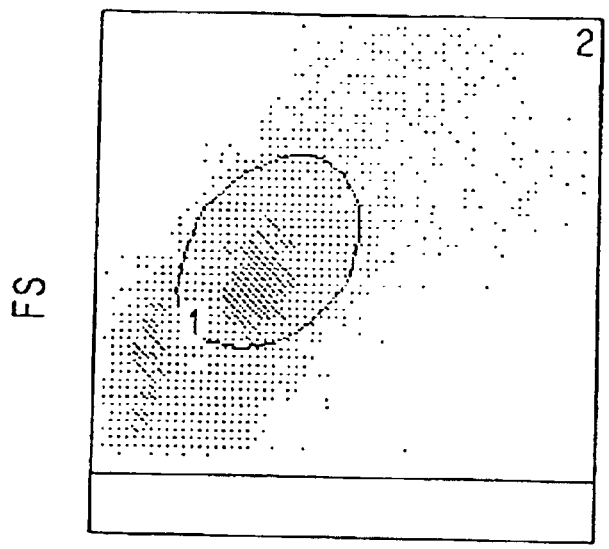
Figure 3B:
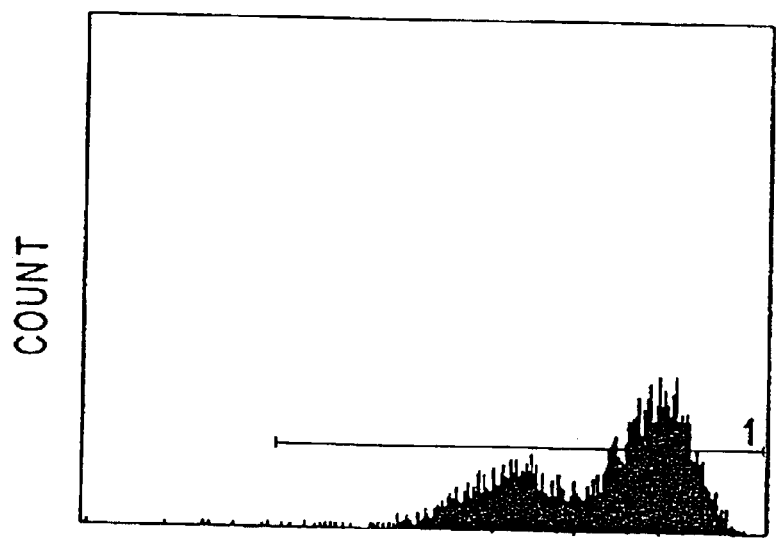

FIGS. 3A and 3B Cytofluorographic analysis of DC stained with antibodies after the first "NYCOPREP 1.068" discontinuous centrifugation followed by antibody panning.

Figure 4:
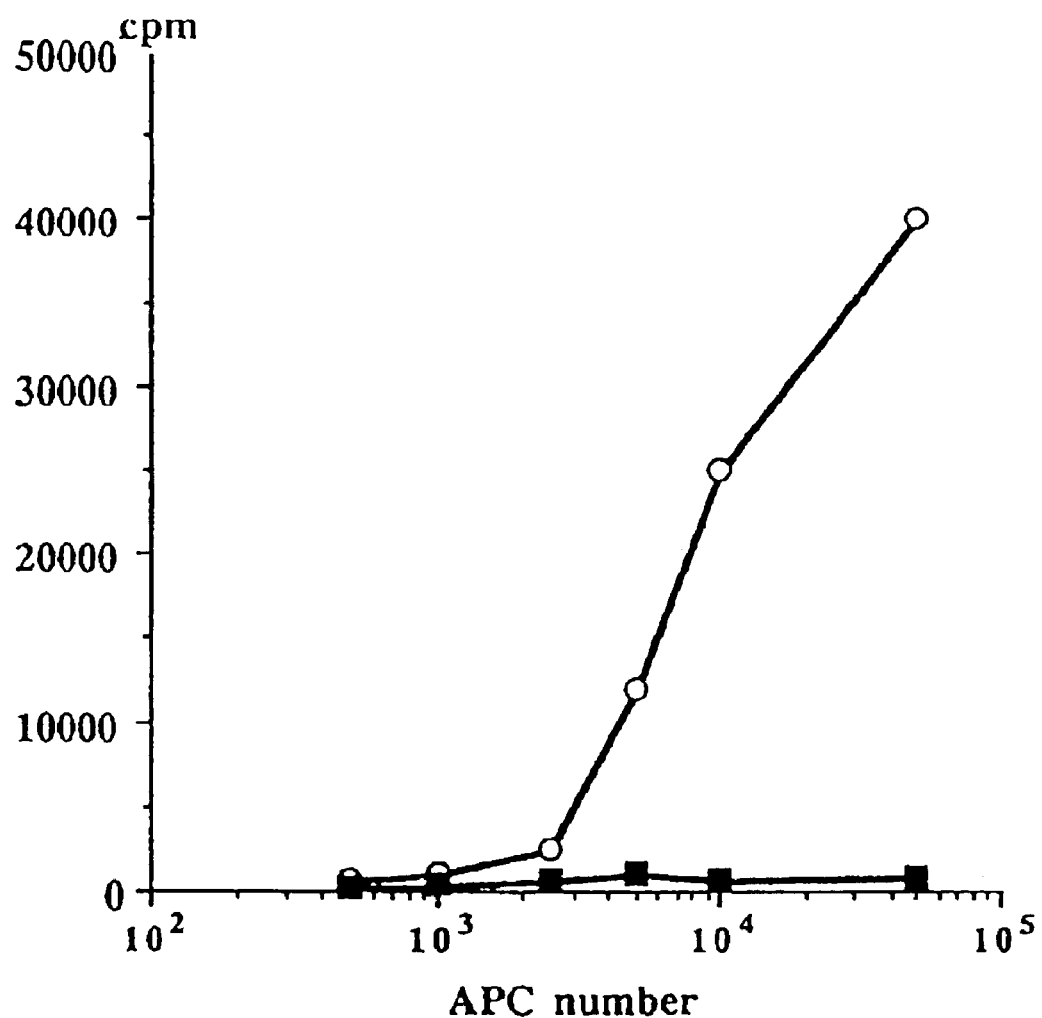

FIG. 4 DC stimulat $\gamma\delta$-TCR$^+$ T cell proliferaton in allogeneic MLR. DC are -○- and monocytes are -■-.

Figure 5A:
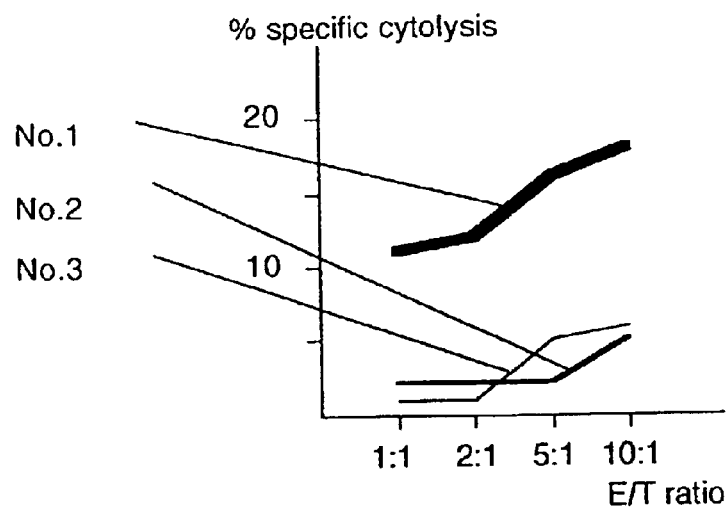
Figure 5B:
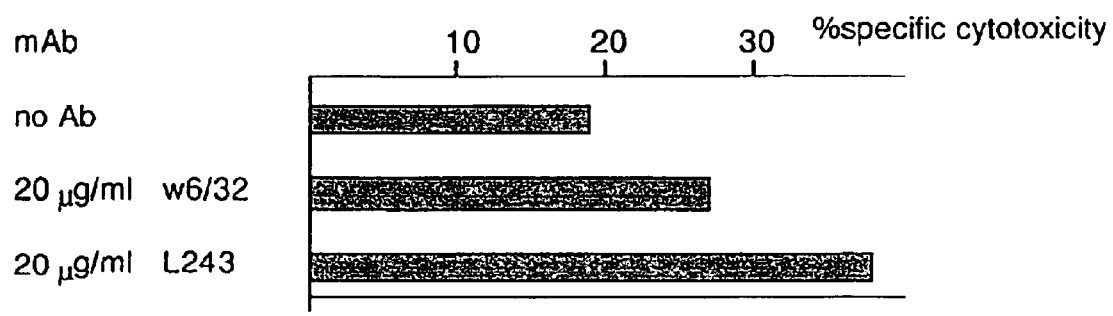

FIGS. 5A and 5B HIV envelope peptide (amino acids 254–274)-pulsed DC activate envelope-specific $\gamma\delta$-TCR$^+$ CTL which lyse peptide-pulsed monocytes in a HLA-unrestricted manner. No. 1=monocytes pulsed with gp120, amino acids 254–274. No. 2=monocytes pulsed with gp120, amino acids 302–323 (control). No. 3=monocytes alone. W6/32 is an anti-HLA class I antibody and L243 is anti-HLA-DR antibody.

Figure 6:
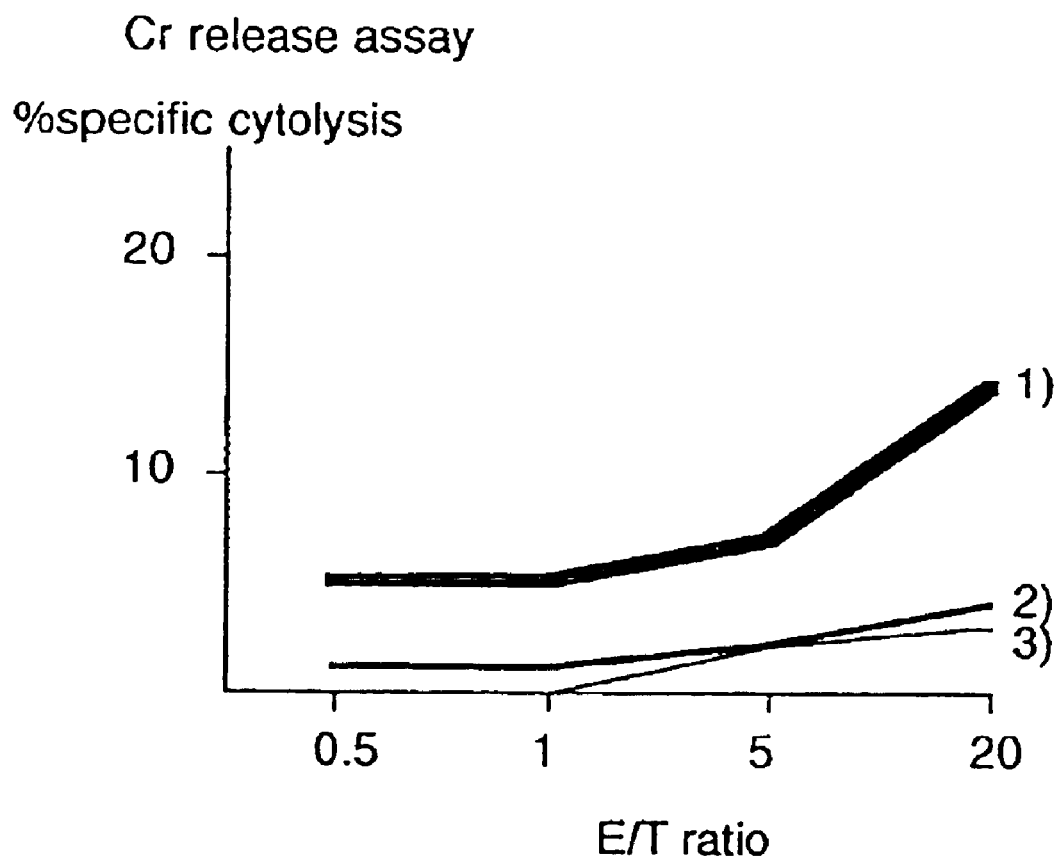

FIG. 6 HIV gag peptide (amino acids 71–85)-pulsed DC activate peptide-specific $\gamma\delta$-TCR$^+$ CTL. 1)=monocytes pulsed with gag, amino acids 71–85. 2)=monocytes pulsed with gp120, amino acids 254–274. 3)=monocytes alone.

Figure 7A:
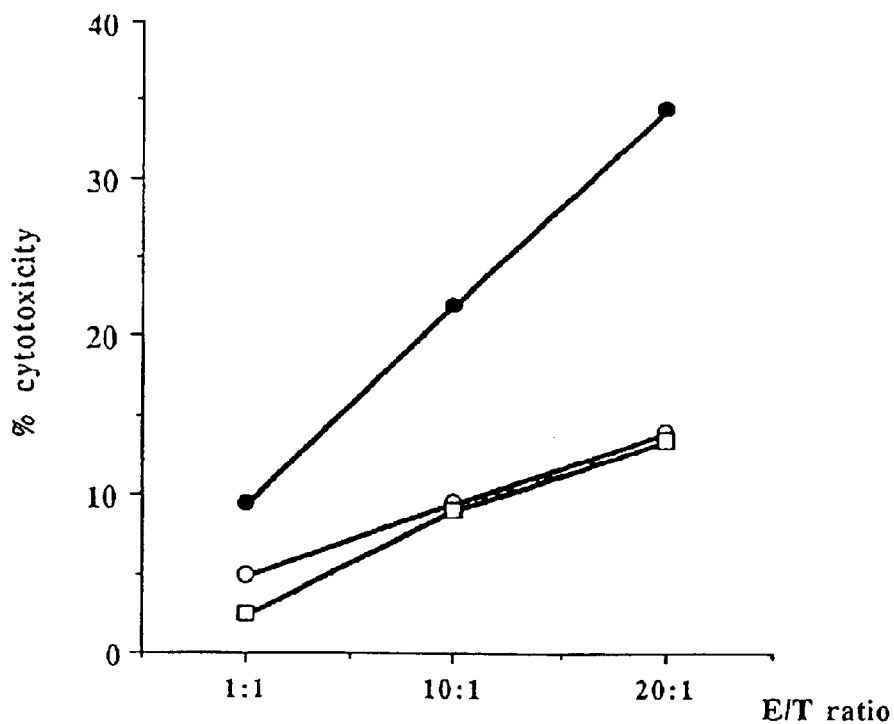
Figure 7B:
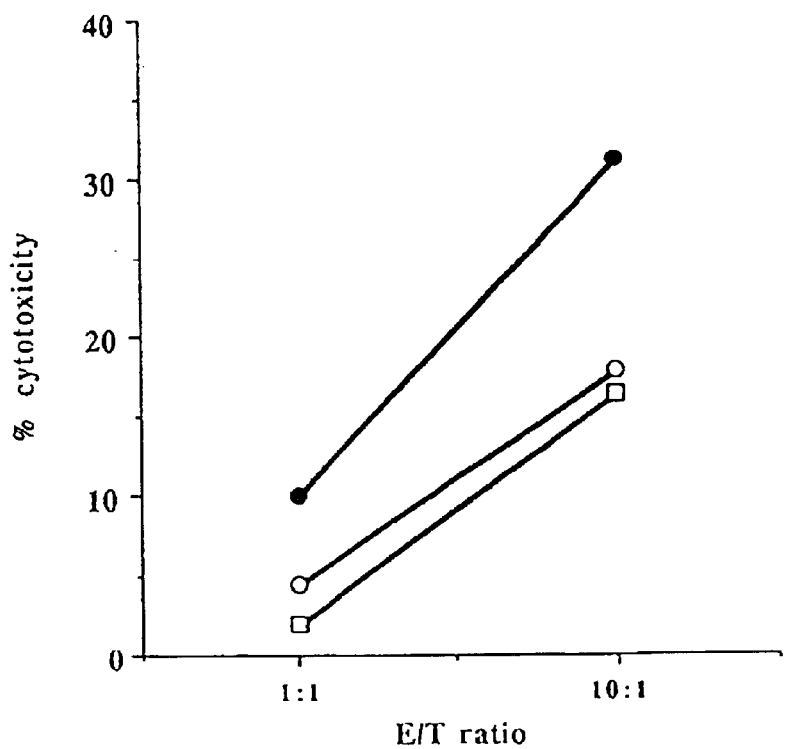

FIGS. 7A and 7B HIV gag peptide (amino acids 21–35)-pulsed DC activate peptide-specific $\gamma\delta$-TCR$^+$ CTL. Monocytes pulsed with gag 21–35 are -●-, monocytes pulsed with gag 71–85 are -□-, and monocytes alone are -○-.

Figure 8:
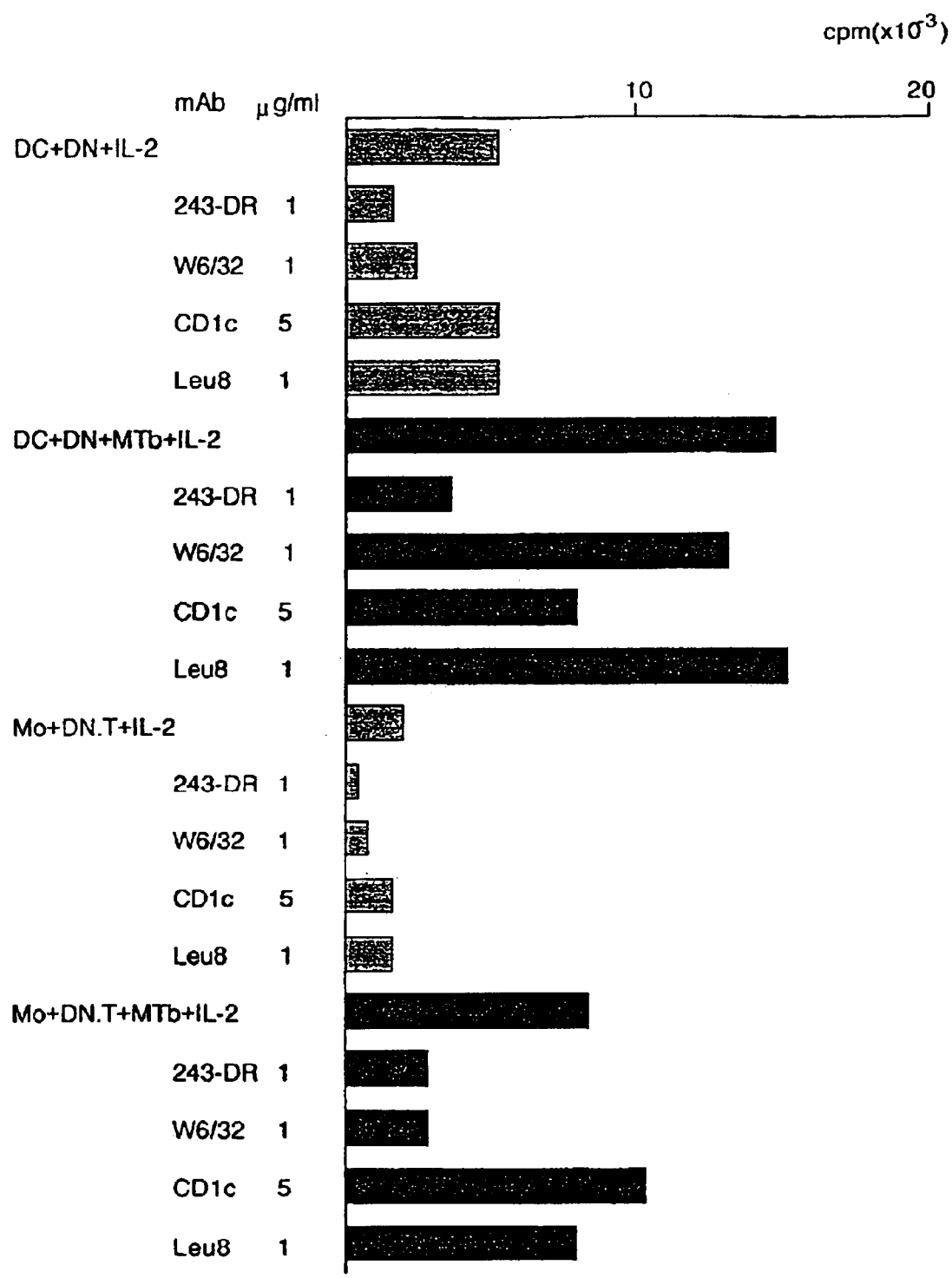

FIG. 8 Antibodies directed to HLA class II determinants and to CD1 molecule inhibit $\gamma\delta$-T cell-mediated proliferation activity in response to *M. tuberculosis* (MTb)-pulsed DC. DN=$\gamma\delta$-T cells, and Mo=monocytes.

Figure 9:
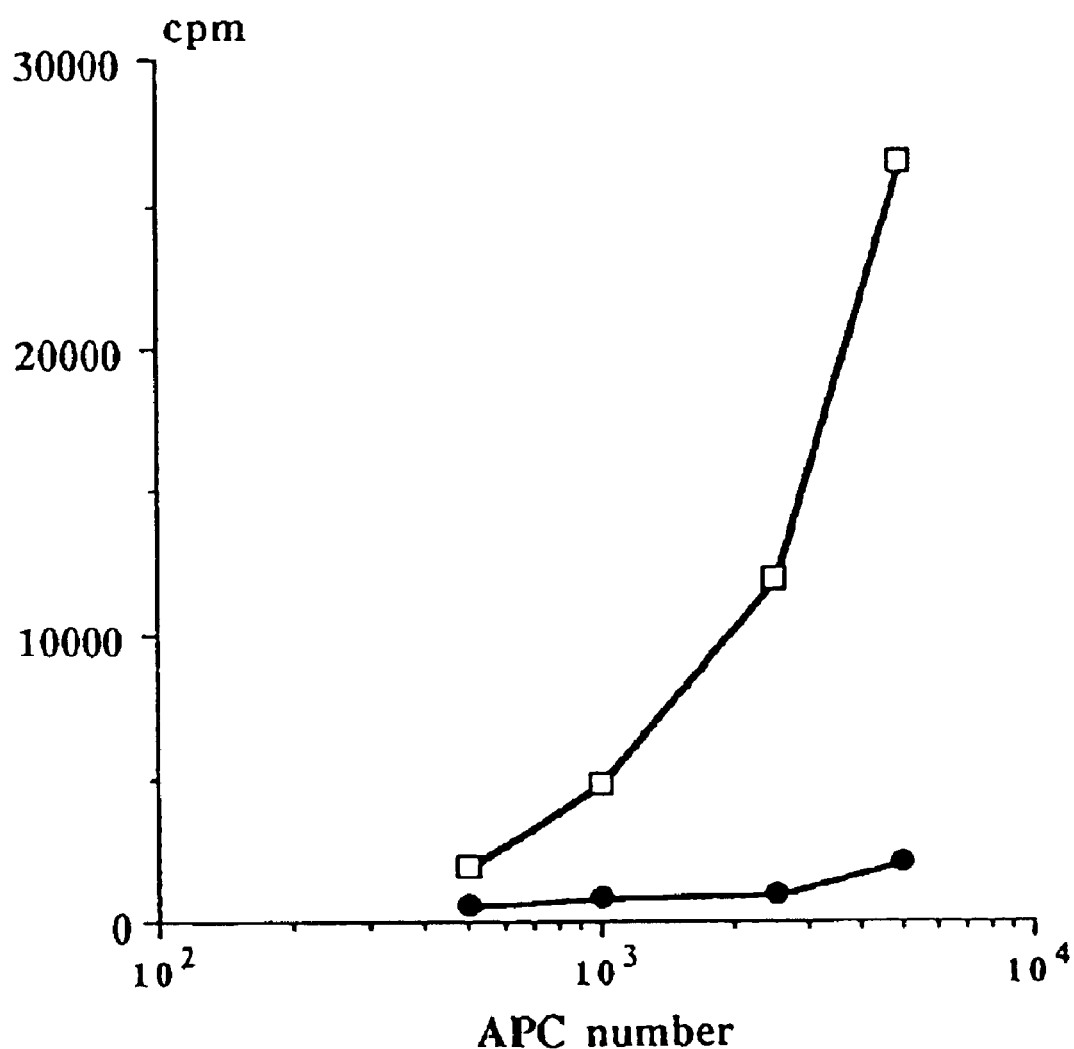

FIG. 9 SAE-A-pulsed DC stimulate $\gamma\delta$-TCR$^+$ T cell proliferation. SAE-A-pulsed DC are -□-, and SAE-A-pulsed monocytes are -●-.

5. DETAILED DESCRIPTION OF THE INVENTION

The present invention relates to methods of isolating and using dendritic cells for activating antigen-specific $\gamma\delta$-TCR$^+$ T cell responses. Although the specific procedures and methods described herein are exemplified using DC and T cells isolated from human blood, they are merely illustrative for the practice of the invention. Analogous procedures and techniques are equally applicable. Therefore, DC may be isolated using variants of the procedure described herein, pulsed with any antigens or fragments thereof, and incubated with primed or unprimed $\gamma\delta$-TCR$^+$ T cells isolated from any tissue where they are found.

5.1. Isolation of Human Blood Dendritic Cells

The present invention relates to an antigen presentation system using DC for the activation of $\gamma\delta$-TCR$^+$ T cells in vitro and in vivo. Due to their presence in low numbers in most tissues, DC must first be isolated and enriched. Although DC are found in both lymphoid and non-lymphoid tissues, a natural and easily accessible source of DC in man is the peripheral blood, which contains an estimate of fewer than 1 DC per 100 white blood cells.

The potency of the accessory cell function of DC in antigen presentation allows for the use of these cells in relatively small numbers when enriched, and absolute purity is not necessary for the generation of a T cell priming effect in vitro. For the in vitro activation of T cells, an APC preparation containing ≧30% DC are generally adequate. However, it is most preferable that a highly purified DC population (>90%) be used for in vivo administration.

Human DC and γδ-T cells may be isolated from any tissues where they reside, using a variety of separation methods. Example 6, infra, presents variants of such methods as illustrations for isolating DC and γδ-TCR$^+$ T cells from the human peripheral blood. This procedure is principally designed to avoid the exposure of DC to antigens such as fetal calf serum, sheep red blood cells and murine monoclonal antibodies which have been used in the separation of peripheral blood leucocytes. Since DC may be able to present such proteins to T cells, even in the absence of other exogenously added antigens, conventional methods of DC isolation may lead to activation of T cells not specific for the antigens of interest, thus potentially masking the response sought. In accordance with this aspect of the invention, human PBML may be isolated from blood samples, particularly buffy coats or leucocytes prepared by apheresis, by "FICOLL HYPAQUE" gradient centrifugation followed by "PERCOLL" discontinuous centrifugation (Markowicz and Engleman, 1990, J. Clin. Invest. 85:955) followed by "METRIZAMIDE" (2-[3-Acetamido-5-N-methyl-acetamido-2,4,6-triiodobenzamido]-2-deoxy-D-glucose) or "NYCOPREP 1.068" NYCODENZ, N.N'-Bis (2,3 dihydroxypropl)-5-[N-(2,3-dihydroxypropyl) acetamido]-2,4,6-trilodo-isophtalamide discontinuous centrifugation. The high buoyant density (HD) fraction contains γ67 and αβ-T cells, B cells, and NK cells, whereas DC are in the low buoyant density (LD) fraction of the "METRIZAMIDE" or "NYCOPREP 1.068". The LD fraction can then be subjected to second "METRIZAMIDE" or "NYCOPREP 1.068" gradient to obtain a further enriched population of DC. DC may also be further enriched using additional protocols, depending on the level of purity required. For use in in vitro activation of T cells, ≧30% DC in an APC preparation can be pulsed immediately with any antigen of interest. The HD cells from the first "METRIZAMIDE" or "NYCOPREP 1.068" gradient can be negatively selected for γδ-TCR$^+$ T cells by panning with monoclonal antibodies directed to markers of αβ-TCR$^+$ T cells, B cells and NK cells for their removal.

Alternatively, DC and γδ-TCR$^+$ T cells may be isolated by procedures involving repetitive density gradient centrifugation, positive selection, negative selection, or a combination thereof. However, the above-mentioned density gradient methods are preferred because they do not contain xenogeneic proteins in the form of mouse antibodies or sheep red blood cells which may be internalized and presented by DC prior to the addition of an exogenous antigen of interest. Positive selection methods may utilize affinity chromatography with antibodies directed to DC or γδ-TCR$^+$ T cell surface markers such as antibodies directed to γδ-TCR (T cell Diagnostics, Cambridge, Mass.). Positive selection does not necessarily require the use of antibodies that recognize DC-specific determinants. For example, B cells and monocytes may be depleted first from the DC-containing fraction after density gradient centrifugation, plastic adhesion, and Fc receptor panning, then an antibody to MHC-Class II antigen can be used to positively select for DC. Negative selection includes modifications of the protocol disclosed herein, supra.

In essence, a DC-containing cell preparation may be reacted with one or more antibodies directed at cell surface antigens not expressed by DC for the removal of non-DC. Antibodies to any T cell, B cell, monocyte, and granulocyte markers may be used. Examples of such antibodies include anti-CD3, anti-CD4, anti-CD5, and anti-CD8 specific for T cells; anti-CD12, anti-CD19 and anti-CD20 specific for B cells; anti-CD14 specific for monocytes; and anti-CD16, and anti-CD56 specific for natural killer cells (Becton Dickinson, San Jose, Calif. and Ortho Diagnostics, NJ). These antibodies may be applied in any combination repeatedly or in a sequential manner for the enrichment of DC. Upon binding to the antibodies, the cells may be removed by adsorption to a solid surface coated with an anti-mouse antibody, as the majority of monoclonal antibodies directed at cell surface markers are of mouse origin, or if the antibodies are conjugated with biotin, the antibody-bound cells can be removed by an avidin or streptavidin-coated surface; or if the antibodies are conjugated to magnetic beads, the cells expressing antigens recognized by the antibodies can be removed in a magnetic field (Harlow and Lane, 1988, Antibodies: A Laboratory Manual, Cold Spring Harbor Laboratory Press).

5.2. Use of Dendritic Cells as Antigen Presenting Cells

The initiation of an immune response is mediated by APC, which process complex antigens into smaller fragments by enzymatic degradation, and present them in association with MHC-encoded molecules to T cells. Although macrophages/monocytes have been studied most extensively as APC, murine DC have been shown to also possess accessory cell function. The present invention demonstrates that DC isolated from human blood present antigens for the activation of antigen-specific γδ-TCR$^+$ T cells in settings where monocytes cannot. Therefore, it provides a method for preparing activated antigen-specific γδ-TCR$^+$ human T cells in vitro by expressing human dendritic cells to an exogenous antigen in vitro, and co-culturing the dendritic cells with γδ-TCR$^+$ human T cells so that the T cells are activated to proliferate or to become cytotoxic in response to the antigen. Such activated T cells may subsequently be used in adoptive immunotherapy. Furthermore, such a method may also be used to identify antigens recognizable by γδ-TCR$^+$ human T cells in order to determine the specific antigenic epitope to which a particular individual is capable of responding prior to its use as a vaccine.

5.2.1. Antigenic Systems for Presentation by Dendritic Cells

The potent accessory cell function of DC provides for an antigen presentation system for virtually any antigenic epitopes which T and B cells are capable of recognizing through their specific receptors. Example 7, infra, demonstrates that human DC can present various protein antigens to isolated γδ-TCR$^+$ T cells. T cell activation is manifested by T cell proliferation and/or cytotoxicity in response to antigen. Hence, DC may be useful in presenting to γδ-TCR$^+$ T cells antigens encoded by infectious agents such as viruses, microorganisms and their products as well as tumor antigens expressed by cancer cells (Urban and Schreiber, 1992, Ann. Rev. Immunol. 10: 617–644).

Infectious agents against which the present invention may be applicable in the induction of a γδ-TCR$^+$ T cell response include, but are not limited to, bacteria, parasites, fungi, and viruses. The multitudes of antigens encoded by these agents, which may be processed and presented by DC include but are not limited to, external surface proteins, and structural proteins including internal enzymes. For example, antigens encoded by any genes of the HIV genome including the env, gag, pol, n f, vif, rev, and tat genes may all be presented by DC to γδ-T cells. In addition, a variety of other infectious agents including hepatitis B virus, hepatitis C virus, cytomegalovirus, herpes simplex virus, varicella zoster, staphylococcal species and Mycobacterium species are encompassed within the scope of the invention.

A large number of human tumor-associated antigens have been identified by monoclonal antibodies (Reisfeld and Cheresh, 1987, Adv. Immunol. 40: 323–377). Although these cellular antigens are selectively expressed in higher quantities by certain tumor cells, it has not been established that they naturally elicit an immune response in cancer patients or can be used effectively to induce such a response. Progress in this area is, in part, hampered by the lack of an adequate in vitro system for analyzing human anti-tumor immune responses, particularly T cell-mediated responses. Unlike animal tumor models in which tumor-reactive T and B cells can be induced through hyperimmunization with tumor cells or tumor antigens, human tumor cells or oncogenic proteins may not be injected into humans for stimulating tumor-reactive T cells due to ethical limitations. Thus, most human studies have utilized lymphocytes obtained from cancer patients whose cells presumably have been exposed to antigens expressed by their autologous tumor cells in vivo. However, it has been shown in some systems that tumor development is accompanied by a down-regulation of tumor specific immune responsiveness mediated by suppressor cells, and if so, T cells isolated from cancer patients may have already come under the influence of such suppression in vivo so as to not function in a manner similar to that of T cells obtained from tumor-immune hosts. Moreover, these attempts to activate human tumor-reactive T cells have generally used monocytes as APC, which are shown herein to be much less effective APC than DC, especially if the T cells have not been primed adequately in vivo against the tumor antigens. Alternatively, cytotoxic lymphocytes have been directly activated by use of high doses of lymphokines such as IL-2, but this approach suffers from a lack of tumor specificity and various toxic side effects.

The DC described herein establish an ideal system for assessing and stimulating human anti-tumor responses, using naive γδ-TCR$^+$ T cells from normal, presumably unsuppressed individuals or γδ-T cells from tumor-bearing patients. The potent accessory cell function of DC may be able to present tumor antigens to γδ-T cells from cancer patients, whose immune response is apparently inadequate to eliminate the tumors in vivo. The activated T cells can be expanded in vitro in the presence of lymphokines such as interleukin 2 and 4 (IL-2 and IL-4) for use in adoptive immunotherapy. Whole tumor cells in viable or irradiated form, tumor membrane preparations, and tumor antigens purified from natural sources or expressed as recombinant products may be used to pulse DC for presentation to γδ-TCR$^+$ T cells.

Recently, oncogene products have been shown to be capable of inducing murine T cell activities. For example, oncogenic forms of the ras gene product p21, and the fusion product p210 of the bcr-abl gene induce T cell proliferative responses, when used to immunize mice (Peace et al., 1991, J. Immunol. 146: 2059–2065; Chen et al., 1992, Proc. Natl. Acad. Sci. USA 89: 1468–1472). Thus, oncogenic proteins which are different from their normal cellular counterparts as a result of amino acid substitutions may possess new immunogenic determinants that are recognizable by γδ-TCR$^+$ T cells. It is not necessary that such proteins be expressed naturally on the cell surface, as cytoplasmic and nuclear proteins may be processed, attached to MHC-encoded products intracellularly, and translocated to the cell surface in a complex form (Gould et al., 1989, J. Exp. Med. 170: 1051–1056). Since oncogene products are expressed in a variety of tumor types including colon cancer, leukemia and lymphoma, DC may be used to activate γδ-TCR$^+$ T cells against such cancers. Human γδ-T cells, particularly cytolytic γδ-T cells specific for oncogene products, may be induced by DC presentation, and expanded by procedures similar to that described herein for the procurement of large numbers of tumor-specific T cells for adoptive cellular immunotherapy in vivo.

Bacterial, parasitic, fungal, viral, and tumor antigens of cellular or viral origin may be introduced to DC by addition to DC cultures, by the osmotic lysis of pinosomes after pinocytotic uptake (Moore et al., 1988, Cell 54: 777–785), or by uptake in antigen containing liposomes. Antigens may be used as purified naturally occurring whole polypeptides, purified recombinant whole polypeptides, whole organisms or cells in viable or dead forms, protein fragments generated by enzymatic digestion, or synthetic peptides produced by solid phase chemical method (Creighton, 1983, Protein Structures and Molecular Principles, W. H. Freeman and Co., N.Y. pp 50–60). The amount of antigens necessary for pulsing DC may vary depending on the nature, size, and purity of the molecules. In general, polypeptides may be used at 1–100 μg/ml, and small peptides at 1–50 μg/ml. Introduction by osmotic lysis of pinosomes requires larger amounts of proteins in the range of 200–500 μg/10$^6$ APC. Alternatively, exogenous genes encoding specific antigens of interest or expression vectors containing such genes or portions thereof may be incorporated into DC in expression vectors using conventional methods, including transfection, recombinant vaccinia viruses and retroviruses (Sambrook et al., 1989, Molecular Cloning: A Laboratory Manual, Cold Spring Harbor Laboratory Press). This approach causes the continual expression of integrated genes, leading to MHC occupancy by the gene products. Any of the aforementioned methods for introducing exogenous antigens into DC as well as any others commonly used by those skilled in the art are hereinafter collectively referred to as pulsing of APC. Antigen pulsing of DC may occur prior to co-culture with γδ-TCR$^+$ T cells or antigens may be added to cultures containing both DC and γδ-T cells at the same time.

5.2.2. Induction of Primary and Secondary T Cell Responses in Vitro

One of the most outstanding characteristics of DC function is their ability to present antigens for the induction of primary T cell responses. Since none of the studies performed in this area have utilized isolated human DC and γδ-TCR$^+$ T cells prior to the present invention, it had not been established that human DC could present exogenous antigens to activate unprimed or primed γδ-T cells. In a specific embodiment by way of example, described in Example 7, infra, naive γδ-TCR$^+$ T cells isolated from individuals not previously exposed to an antigen can be primed in vitro by DC pulsed with that antigen. Antigen-pulsed DC activate both proliferative and cytolytic γδ-T cell responses. This is in contrast to monocyt s which are only competent antigen presenters in vitro to already primed T cells for secondary responses.

For the induction of a primary T cell response in vitro, DC may be used immediately after antigen pulsing or they may be maintained in the presence of GM-CSF and/or other cytokines prior to antigen pulsing and co-culture with γδ-TCR$^+$ T cells (Markowicz and Engleman, 1990, J. Clin.Invest.85:955). It is known that although DC may process antigens for only a short time period in vitro, they retain the antigenic fragments bound to MHC molecules for a significant time period, and thus, may be used even several days after antigen pulsing (Inaba et al., 1990, J. Exp. Med. 172: 631–640).

In order to augment the magnitude of the priming effects of DC, exogenous lymphokines and monokines may be added to the cultures, including but not limited to, GM-CSF and IL-2, at 0.1–100 U/ml. Higher concentrations of such cytokines may also be used; however, they may induce antigen non-specific T cell activities. It is not required that any exogenous factors be present, since DC appear to produce all the necessary signals for T cell activation. However, for the long-term expansion of T cells after DC priming, lymphokines such as IL-2, IL-4 and IL-7 at 1–100 U/ml may be used to greatly facilitate the rate at which γδ-T cells propagate.

γδ-TCR$^+$ T cells may be obtained from various tissues for use as responder cells. Such tissues include but are not limited to, gut, skin, spleens, lymph nodes, and peripheral blood. The cells may be co-cultured with antigen-pulsed DC as a mixed population or as a purified subset, depending on the type of response and/or the composition of the stimulated cells desired. However, since γδ-TCR$^+$ T cells represent a minor population of total T cells, it is preferred that γδ-T cells are first enriched prior to co-culture with DC; otherwise, a γδ-T cell response may be overwhelmed by a concomitant a αβ-T cell response. For example, in a culture designed to generate HIV-specific γδ-TCR$^+$ T cells, CD4$^+$ T cells may be depleted prior to culture since they are susceptible to HIV infection. Thus, it may be more desirable to culture purified γδ-TCR$^+$ T cells with DC pulsed with HIV antigens to generate HIV-specific γδ-T cells. This is particularly important if γδ-TCR$^+$ T cells are obtained from HIV-infected patients for restimulation and expansion in vitro, the depletion of CD4$^+$ and CD8$^+$ T cells reduces the likelihood of HIV contamination of cultures. In addition, early elimination of CD4$^+$ T cells prevents the overgrowth of CD4$^+$ cells in a mixed culture of both CD4$^+$ and γδ-TCR$^+$ T cells over time. It is demonstrated in Example 7, infra, that antigen-specific γδ-TCR$^+$ cytolytic T cells can be induced in the absence of detectable CD4$^+$ T cells, when stimulated with antigen-pulsed DC. T cell purification may be achieved by positive, or negative selection, including but not limited to, the use of antibodies directed to CD2, CD3, CD4, CD5, CD8, αβ-TCR and γδ-TCR as shown in Example 6, infra.

γδ-TCR$^+$ T cells may be isolated from an individual not previously exposed to a particular antigen. Antigen-pulsed DC may be used also to reactivate previously primed γδ-TCR$^+$ T cells for a secondary response, in which case, the donors may be tested first for prior antigen exposure by the presence of serum antibodies or a detectable T cell response. Antigen-pulsed DC not only sensitize naive T cells but they also stimulate a stronger secondary T cell response in vitro than monocytes can.

Once naive γδ-TCR$^+$ T cells have been activated by DC, they may be restimulated by any APC including autologous DC, autologous normal or Epstein Barr Virus-transformed B cells, or monocytes, and expanded with lymphokines. The expanded γδ-TCR$^+$ T cells may be administered alone into an individual, or in combination with lymphokines such as IL-2 and/or IL-4, by repeated injections or continuous infusion via any conventional route.

The use of DC to activate γδ-TCR$^+$ T cells depends on a number of conditions. For example, patients with late stage HIV infection may not be able to generate competent anti-viral γδ-TCR$^+$ T cell responses, and thus, γδ-TCR$^+$ T cells from healthy HLA-matched or mismatched individuals, may be primed with HIV antigen-pulsed DC in vitro, expanded in numbers, and administered into the patients. The observation that the in vitro primed γδ-TCR$^+$ T cells are capable of lysing antigen-pulsed target cells even in the presence of MHC-class I and class II molecule-specific antibodies indicates that γδ-TCR$^+$ cytolytic T cells may be used in adoptive immunotherapy to effectively eradicate MHC-mismatched antigen-positive or virally-infected cells in a recipient. The effects of therapy can be monitored on the basis of changes in viral load, the number of CD4$^+$ T cells in the patients' blood, and clinical course. On the other hand, HIV-infected patients with early-stage disease may still possess γδ-TCR$^+$ T cells capable of becoming HIV-specific cytolytic cells. In this case, the proposed treatment may involve ex vivo re-activation of their own γδ-TCR$^+$ T cells by autologous or HLA-matched or even HLA-mismatched antigen-pulsed DC followed by reinfusion of their own activated T cells. A similar approach may be applicable in other viral infections and in cancer patients, depending on the stage of the disease, the need for HLA-matched donor cells, and the ability of the patients' own T cells to mount a competent antigen-specific immune response.

5.2.3. Induction of Primary and Secondary T Cell Responses in Vivo

The ability of DC to process and retain antigenic fragments for several days permits their use as potent immunogens in vivo. DC may be pulsed with antigens according to the various methods described in Section 5.2.1, supra, washed, and administered in vivo as vaccines and/or immunotherapeutics for the elicitation or augmentation of a pre-existing but weak γδ-TCR$^+$ T cell response. It is possible that immunization with antigen-pulsed DC can increase both the magnitude and the specificity of a response. It may be desirable to repeat such immunizations at time intervals of days or weeks. The potency of DC as APC may alleviate the need of using conventional adjuvants to augment the response, although it does not preclude the use of adjuvants to further enhance immune reactivity. Antigen-pulsed DC may be used to prime and/or boost γδ-TCR$^+$ T cell-mediated responses in vivo against infectious agents and cancer.

5.2.4. A Method for Identification of Immunogenic Peptides

Currently, the conventional methods for assessing immunogenicity of proteins involve the immunization of animals with the proteins or fragments thereof, and subsequently testing for their secondary T cell or antibody responses in vitro or in vivo. The requirement of an in vivo priming step is both labor-intensive and time-consuming. In addition, an immune response to an antigen mounted by an animal host is not necessarily correlative to a human immune response to the same antigen. The ability of DC to induce primary γδ-TCR$^+$ T cell responses in vitro alleviates the need for in vivo animal priming. γδ-TCR$^+$ T cells may be obtained from any individuals with or without previous antigen exposure and tested for their recognition of defined epitopes presented by DC.

The DC antigen presentation system involves the culturing of γδ-TCR$^+$ T cells with autologous or HLA-matched or even HLA-mismatched DC in the presence of any antigen. Antigens may be introduced through gene transfer using infectious viral vectors or used in recombinant form or purified from natural sources, in whole or in part. Both γδ-TCR$^+$ T cell proliferative and cytotoxic activities can be measured. Although the HIV peptides shown in Example 7, infra, have been known to elicit antibody responses, they were not known to be targets of γδ$^+$ T cell responses. This system provides for a rapid method for analyzing and mapping γδ-TCR$^+$ T cell reactivities with various antigenic epitopes by any individuals, thereby facilitating the design of "tailor-made" vaccines based on each individual's own immune repertoire and pattern of γδ-TCR$^+$ T cell recognition. It further allows the comparison of the magnitude of γδ-TCR$^+$ T cell responses to different epitopes, thereby identifying immunodominant epitopes for γδ-TCR$^+$ T cells for the induction of the strongest immune response.

6. EXAMPLE

Isolation and Purification of Dendritic Cells from Human Peripheral Blood

6.1. Materials and Methods

6.1.1. Cell Separation

Human DC and γδ-TCR$^+$ T cells were obtained from buffy coats of healthy, HIV-1 seronegative donors. Peripheral blood mononuclear leucocytes (PBML) were isolated by "FICOLL-HYPAQUE" gradient centrifugation (Boyum, 1968, Scand. J. Clin. Lab. Invest: 21:21–29). In brief, a buffy coat was diluted with Dulbecco's PBS without divalent ions such as Ca$^{2+}$ or Mg$^{2+}$ (referred to as DPBS) up to 10 ml. 10 ml of "FICOLL" was gently underlaid into each tube and centrifuged at 1000×g for 35 minutes at room tempeature. The interface was collected and washed with DPBS three times.

To separate monocytes from the remaining mononuclear cells, the preparation was further fractionated over a four layer discontinuous "PERCOLL" gradient (30%, 40%, 50.5% and 75%) (Pharmacia, Uppsala, Sweden) (Markowicz and Engleman, 1990, J. Clin. Invest. 85:955). Original "PERCOLL" density was prepared at 1.130 g/ml DPBS and 15 ml of a 50.5% "PERCOLL" solution was made and shaken in a conical polypropylene tube to create a foam on a surface of the "PERCOLL" solution. THe tube was gently underlaid with about 6.5 ml of 75% "PERCOLL". The tube was then slowly overlaid with 3 to 3.5 ml of 40% "PERCOLL" dropwise along the side of the tube which was being slowly rotated, followed by an overlay of 2.5 ml of 30% "PERCOLL" in the same manner. The gradients were kept on ice for use within about 4 hours.

2.5–3×10$^8$ PBML in 5 to 10 ml of DPBS supplemented with 5% human serum were overlaid onto the four layer discontinuous "PERCOLL" gradient. The cells were centrifuged at 1000×g for 20–25 minutes at 4° C. The LD cells (monocytes) were collected from the interface over the "PERCOLL" 50.5% layer, whereas the lymphocytes and DC were collected from the interface between 75% and 50.5% layers. The collected cell fractions were diluted with DPBS at least 3 volumes and centrifuged at 1000×g for 12 minutes at 4° C. The cells were washed twice with DPBS supplemented with 5% human serum at 400×g for 5–6 minutes at 4° C.

The HD cells (3–7×10$^8$/50 ml of RPMI containing 10% pooled human serum) were then cultured overnight in teflon vessels at 37° C. Thereafter, the cultured cells were subjected to gradient centrifugation in "METRIZAMIDE" (15.5%) by overlaying the cells onto 10 ml of 15.5% (wt/vol) "METRIZAMIDE" (Sigma Chemical Co.) followed by centrifugation at 650×g for 10 min at room temperature. This fraction was further depleted of contaminating monocytes by a solid phase absorption procedure on human IgG-coated petri dishes. The DC were then enriched over a second "METRIZAMIDE" gradient (14%). The HD cells from the first "METRIZAMIDE" gradient consisted of a mixture of αβ and γδ-T cells, B cells, and NK cells were enriched for γδ-T cells by "negative panning", during which the cells were incubated on plastic petri dishes previously coated with a mixture of monoclonal antibodies anti-CD4 (Leu 3a), anti-CD8 (Leu 2a), anti-CD16 (Leu 11c), anti-CD19 (Leu 12), and anti-HLA-DR (CA141) (Engleman et al., 1981, J. Immunol. 127:2124–2129). Many of such antibodies were available through the American Type Culture Collection. αβ-T cells bound to the petri dish because nearly all such cells expressed either CD4 or CD8; NK cells also bound because of th ir expression of CD16, and B cells bound because of their expression of CD19 and HLA-DR. If any activated T cells were present in this mixture, they would also bind to the petri dish by virtue of their expression of HLA-DR. In principle, the only cells that did not bind to the dish were γδ-TCR$^+$ double negative (CD4$^-$ and CD8$^-$) T cells. The purity of the DC and γδ-TCR$^+$ T cells obtained using this procedure were 60–90% and 70–80%, respectively, and the contamination of CD4$^+$ and CD8$^+$ T cells was less than 1% as assessed by flow cytometry.

Alternatively, the DC could be enriched after overnight culture by centrifugation over a "NYCOPREP 1.068" discontinuous gradient (Nycomed Pharma AS, Olso, Norway). About 2.5×10$^8$ cells were suspended in 15–20 ml of a solution made up of 85% DPBS, 10% human serum and 5% EDTA. This was underlaid sequentially with 4–5 ml of a solution of 50% human serum, 10% EDTA and 10% DPBS, followed by 4 ml of a solution of 75% "NYCOPREP 1.068", 24% DPBS and 1% human serum, followed by 8 ml of 100% "NYCOPREP 1.068". The cells were centrifuged at 400×g for 13 minutes at room temperature. The interface and the pellet were collected and diluted with at least 3 volumes of DPBS containing lot human serum, and centrifuged at 800×g for 12 minutes at 20° C. The cells were washed twice with 10% human serum in RPMI at room temperature, and DC occupied 30–40% of the total cell population. However, these cells could be further enriched by another round of "NYCOPREP" centrifugation to obtain a LD fraction of 80–90% DC. Alternatively, the LD cells after the first "NYCOPREP" step could be negatively selected by incubation with antibody-coated petri dishes to remove CD3$^+$, CD14$^+$, CD16$^+$ and CD20$^+$ cells. The non-adherent cell population also contained 80–90% DC. However, it is preferred that density gradient centrifugation was used exclusively to avoid the presence of xenogeneic proteins in the form of antibodies against leukocyte markers. All procedures described herein could produce a yield of 1–2.5×10$^6$ cells from 400–500 ml of whole blood.

The purity of DC following each step of DC enrichment was assessed by staining with an anti-HLA-DR (anti-MHC class II) antibody (CA141) conjugated to fluorescein, and phycberythrin-conjugated anti-CD14 (anti-monocyte). Cytofluorographic analysis of the entire cell population was assessed by Fluorescence Activated Cell Sorter. HLA-DR$^+$ but CD14$^-$ cells represented the DC population.

6.2. EXAMPLES

6.2.1. Isolation of Highly Purified Peripheral Blood Dendritic Cells

Highly purified DC were obtained using a combination of density gradient centrifugation procedures, and/or antibody panning steps. The purity of DC was monitored using a monoclonal antibody specific for HLA-DR (MHC class II) antigens, since DC specific antibodies were not available. DC can be readily distinguished from other PBML on the basis of their high level expression of MHC-class II determinants and their concurrent lack of CD14 expression, which was associated with monocytes. The brightly staining MHC-class II$^+$ DC were also negative for a variety of known T, B, and NK cell markers.

For example, at the end of the first "NYCOPREP 1.068" discontinuous centrifugation step, the LD fraction contained 30–40% DC as determined by the presence of HLA-DR$^+$ and CD14$^-$ cells (FIGS. 1A and 1B). The DC fraction could be further enriched by a second "NYCOPREP 1.068" discontinuous centrifugation (FIGS. 2A and 2B), or by panning with monoclonal antibodies specific for non-DC markers (FIGS. 3A and 3B). These procedures described herein gave rise to a highly purified population of 80–90% DC. A similar result was also obtained using "METRIZAMIDE" centrifugation.

7. EXAMPLE

Generation of Antigen-specific γδ-TCR$^+$ T Cells Using Dendritic Cells

7.1. Materials and Methods

7.1.1. Antigens and Reagents

HIV envelope gp120 peptide from amino acid 254 to 274 (Ho et al., 1988, Science 239:1021) derived from a conserved region of the protein and gag p17 peptide from amino acid 21 to 35 or from 71 to 85 (Nixon and McMichael, 1991, AIDS 5:1049) were synthesized on an automated peptide synthesizer and their purity was assessed by HPLC and amino acid analysis. *M. tuberculosis* extract was obtained from Dr. Mohagheghpour at Kuzell Institute of Arthritis and Infectious Diseases. Monoclonal antibodies directed to the CD1c molecule were purchased from AMAC, Inc. *Staphylococcal aureus* enterotoxin-A superantigen was purchased from Sigma Chemical Co.

7.1.2. T Cell Cultures

For the induction of a γδ-T cell-mediated response, HIV envelope gp120 peptide or gag p17 peptides was added to isolated DC at 5–10 μg/ml for 2 hours. Afterwards, partially enriched autologous γδ-TCR$^+$ T cells were added at a ratio of 10 such cells to every 1 DC in a total volume of 1 ml of medium in 48-well microliter wells. The incubation medium was RPMI 1640 medium supplemented with 10% heat inactivated pooled human serum, 2mM L-glutamine, 100 μg/ml streptomycin, and 100 U/ml penicillin. Typically, the starting population consisted of $10^4$–$10^5$ DC and $10^4$–$10^6$ γδ-TCR$^+$ T cells. These preparations were cultured at 37° C. in a standard 10% $CO_2$ in air, humidified incubator and on the fourth day of culture 10–20 U/ml of recombinant IL2 was added to the cultures. On the seventh day, the cultures were restimulated with autologous monocytes which had been incubated for 2 hours with the same antigenic peptide used for the primary stimulation. The expanded cells were harvested after a total of 14–18 days incubation, and standard 4 hour $^{51}$Chromium (Cr) release assays were performed to determine if the γδ-T cells could lyse antigen-pulsed autologous monocytes.

7.1.3. Proliferation Assay

γδ-TCR$^+$ T cells from normal human peripheral blood were cultured with autologous DC or monocytes pulsed with *M. tuberculosis* extract as antigen for 7 days. Prior to co-culture with T cells, DC or monocytes were preincubated with 5 μg/ml *M. tuberculosis* extract for 20 hrs. The proliferative response was assessed by [$^3$H]-thymidine incorporation (Mohagheghpour et al., 1987, J. Immunol. 138:570). For antibody blocking experiments, the antibody was added to DC or monocyte culture at the beginning of preincubation with antigen. IL-2 was added at 5 u/ml/well on day 4. In addition, γδ-T cells were cultured with autologous DC or monocytes in the presence of 5 ng/ml of SAE-A for 4 days without any IL-2.

7.1.4. Cytotoxicity Assay

After approximately 2–3 weeks, the resultant γδ-TCR$^+$ T cells were analyzed for cytotoxicity activitin a standard $^{51}$Cr release assay. Target cells were $^{51}$Cr labelled autologous monocytes which were either untreated or pulsed with HIV envelope peptide or gag peptides. In antibody blocking experiments, the different MAbs were added at 20 μg/ml to the cultures in the $^{51}$Cr release assay. Spontaneous $^{51}$Cr release from target cells in the absence of CTL was <15%. Percentage specific $^{51}$Cr release from lysed target cells was calculated as:

$$\frac{100 \times [\text{cpm(sample release)} - \text{cpm(spontaneous release)}]}{[\text{cpm(total release)} - \text{cpm(spontaneous release)}]}$$

7.2. EXAMPLES

To examine the direct interaction between the APC (DC, monocytes and B cells) and γδ-T cells, autologous and allogeneic MLR were performed. In both types of MLR, DC alone could induce the proliferative response of γδ-T cells while monocytes could not (FIG. 4). In blocking experiments of allogeneic MLR, anti-γδ TCR MAb inhibited the proliferation (80% inhibition), but anti-CD4 and -CD8 MAb did not. Interestingly, anti-B7 and anti-CD28 MAb inhibited the proliferative response of γδ-T cells 2- to 3-fold more than that of CD4$^+$ αβ-TCR$^+$ T cells, suggesting that these adhesion molecules played a role in the activation of γδ-T cells.

In order to test the ability of human DC to present exogenous antigens to γδ-TCR$^+$ T cells, DC and γδ-T cells were isolated from human blood and co-cultured in the presence of several antigens. The experiments described below utilized DC isolated by "FICOLL", "PERCOLL" and "METRIZAMIDE" density gradient centrifugation. However, DC obtained by "NYCOPREP 1.068" or other methods known in the art could be used as well. The results indicated that several γδ-T cell lines generated by culturing γδ-TCR$^+$ T cells with HIV peptide-pulsed DC lysed autologous monocytes that had been pulsed with HIV peptides, but not autologous monocytes that had not been pulsed with peptide or monocytes pulsed with a different peptide from that used for primary stimulation in vitro (FIGS. 5A and 5B, 6, and 7A and 7B). Monoclonal antibodies to HLA class I and DR determinants that were known to inhibit HLA class I and class II-restricted CTL activity of αβ-T cells, failed to inhibit γδ-T cell mediated-HIV specific cytotoxicity, indicating that the antigen-specific cytolytic activity by the γδ-T cells was not HLA class I or HLA class II restricted (FIG. 5B).

In other experiments, DC pulsed with an extract of *M. tuberculosis* were shown to stimulate fresh autologous γδ-TCR$^+$ T cells to proliferate, and such proliferation was inhibited by MAbs to HLA class II determinants and to the CD1c molecule (FIG. 8). *M. tuberculosis* extract-pulsed monocytes also stimulated autologous γδ-T cells to proliferate; however, this response might be a secondary response of γδ cells previously primed in vivo. Double negative γδ-T cells were stimulated to proliferate by DC pulsed with SAE-A (FIG. 9). Interestingly, the γδ-T cell responses described herein in autologous MLR, to *M. tuberculosis* and to various HIV peptides required the addition of IL-2 in the cultures, whereas allogeneic MLR and the response to SAE-A did not.

In conclusion, the working examples show that DC could present a variety of antigens to γδ-TCR$^+$ T cells. The methods exemplified herein can be used to identify antigens and antigenic peptides that are recognized by γδ-T cells and stimulate the growth of antigen-specific subpopulations of γδ-T cells. The antigenic epitopes identified in this manner may be useful in the design of subunit vaccines against infectious agents. These results also point to the possibility of using antigen-pulsed DC cells to stimulate the proliferation and generation of antigen-specific γδ-TCR$^+$ lines, which can be used for purposes of adoptive immunotherapy. For example, γδ-TCR$^+$ T cells specific for HIV can be used to treat HIV infected individuals, in whom such T cells would be expected to lyse HIV-infected cells and, thereby, reduce viral load. Since γδ-T cells, in contrast to αβ-T cells, predominate in the skin and reproductive tract as well as lung and intestine, they may have advantages over αβ-T cells in combating infection at these sites. Since the antigen-specific γδ-T cells appear to be HLA-unrestricted, it may be possible to utilize the cells of one individual to treat disease in another individual of different HLA types. Furthermore, the results also indicate that it should be possible to generate γδ-TCR$^+$ T cells to a variety of antigens, including tumor-associated antigens as. well as antigens associated with infectious pathogens.

The present invention is not to be limited in scope by the exemplified embodiments which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for preparing activated antigen-specific γδ-T cell receptor-positive human T cells in vitro comprising exposing human dendritic cells to an exogenous antigen in vitro, and co-culturing in vitro the dendritic cells with uncloned CD4 negative, CD8 negative (double negative) γδ-T cell receptor-positive human T cells, which T Cells have been enriched from a natural cell source, so that the γδ-T cell receptor-positive T cells are activated to generate cytotoxic T cells specifically reactive to cells that express the antigen and said activation is not MHC restricted.

2. The method of claim 1 in which the antigen is a virus.

3. The method of claim 2 in which the virus is human immunodeficiency virus.

4. The method of claim 1 in which the antigen is a polypeptide.

5. The method of claim 1 in which the antigen is a peptide.

6. The method of claim 5 in which the peptide is derived from human immunodeficiency virus.

7. The method of claim 1 in which the dendritic cells are isolated from human peripheral blood.

8. A method for preparing activated antigen-specific γδ-T cell receptor-positive human T cells in vitro comprising exposing human dendritic cells to an exogenous antigen in vitro, and culturing in vitro the dendritic cells with uncloned double negative γδ-T cell receptor-positive human T cells, which T cells have been enriched from a natural cell source, so that the γδ-T cell receptor-positive T cells proliferate in response to said antigen, and said activation is not MHC restricted.

9. A method for generating antigen specific cytotoxic T cells from uncloned double negative γδ-T cell receptor-positive human T cells in vitro, comprising:

(a) isolating dendritic cells from human peripheral blood;

(b) exposing said human dendritic cells to an exogenous antigen in vitro;

(c) selecting an uncloned population of double negative γδ-T cell receptor-positive human T cells from a natural cell source; and (d) co-culturing said exposed human dendritic cells with said uncloned γδ T cells, wherein said γδ T cells are activated to yield antigen specific cytotoxic T cells and said activation is not MHC restricted.

10. The method of claim 9, wherein the γδ-T cell receptor positive T cells have not previously been exposed to said antigen and the generation of antigen specific cytotoxic T cells is a primary immune response.

11. The method of claim 9, wherein the γδ-T cell receptor positive T cells have been previously exposed to said antigen and the generation of antigen specific cytotoxic T cells is a secondary immune response.

* * * * *

UNITED STATES PATENT AND TRADEMARK OFFICE
CERTIFICATE OF CORRECTION

PATENT NO.    : 6,821,778 B1
DATED         : November 23, 2004
INVENTOR(S)   : Edgar G. Engleman et al.

It is certified that error appears in the above-identified patent and that said Letters Patent is hereby corrected as shown below:

<u>Column 1,</u>
Line 7, insert the following paragraph:

-- This work was supported in part by The National Institutes of Health Grants CA 24607 and AI 25922. Accordingly the United States government may have certain rights in this invention. --.

Signed and Sealed this

Eleventh Day of April, 2006

JON W. DUDAS
*Director of the United States Patent and Trademark Office*